United States Patent [19]

Brooker, Jr.

[11] Patent Number: 4,865,608

[45] Date of Patent: Sep. 12, 1989

[54] GROOVED ENDOPROSTHESIS

[76] Inventor: Andrew F. Brooker, Jr., 4 Merrion Ct., Timonium, Md. 21093

[21] Appl. No.: 123,399

[22] Filed: Nov. 20, 1987

[51] Int. Cl.4 .............................................. A61F 2/32
[52] U.S. Cl. ........................................ 623/23; 623/18
[58] Field of Search ........................ 623/16, 18, 22, 23

[56] References Cited

U.S. PATENT DOCUMENTS

| 2,719,522 | 10/1955 | Hudack | 623/23 |
|---|---|---|---|
| 3,067,740 | 12/1962 | Haboush | 623/23 |
| 3,894,297 | 7/1975 | Mittelmeier et al. | 623/23 |
| 4,021,865 | 5/1977 | Channley | 623/23 |
| 4,031,571 | 6/1977 | Heimke et al. | 623/23 |
| 4,163,292 | 8/1979 | Averett, Jr. | 623/23 |
| 4,199,824 | 4/1980 | Niederer | 623/23 |
| 4,231,120 | 11/1980 | Day | 623/23 |
| 4,259,072 | 3/1981 | Hirabayashi et al. | 623/23 |
| 4,272,855 | 6/1981 | Frey | 623/23 |
| 4,310,931 | 1/1982 | Müller | 623/23 |
| 4,385,405 | 5/1983 | Teinturier | 623/23 |
| 4,404,693 | 9/1983 | Zweymüller | 623/23 |
| 4,407,022 | 10/1983 | Heimke et al. | 623/23 |
| 4,430,761 | 2/1984 | Niederer et al. | 623/23 |
| 4,435,854 | 3/1984 | Keller | 623/23 |
| 4,623,349 | 11/1986 | Lord | 623/23 |
| 4,661,112 | 4/1987 | Müller | 623/23 |
| 4,664,668 | 5/1987 | Beck et al. | 623/23 |
| 4,673,409 | 6/1987 | Van Kampen | 623/23 |
| 4,704,128 | 11/1987 | Frey | 623/23 |
| 4,714,470 | 12/1987 | Webb, Jr. et al. | 623/23 |

FOREIGN PATENT DOCUMENTS

| 0169976 | 2/1986 | European Pat. Off. | 623/22 |
|---|---|---|---|
| 2324865 | 11/1974 | Fed. Rep. of Germany | 623/23 |
| 0560042 | 3/1975 | Fed. Rep. of Germany | 623/23 |
| 2551013 | 5/1976 | Fed. Rep. of Germany | 623/23 |
| 2549718 | 2/1985 | France | 623/22 |
| 2069340 | 8/1981 | United Kingdom | 623/23 |

Primary Examiner—Richard J. Apley
Assistant Examiner—David J. Isabella
Attorney, Agent, or Firm—Barnes & Thornburg

[57] ABSTRACT

An implantable prosthesis has a plurality of grooves formed on a surface to promote biological fixation to the surrounding tissue. The grooves are preferably substantially equal in width, depth and spacing. The width of the grooves ranges from 350–535 microns, and the depth ranges from 380–635 microns. The spacing between adjacent grooves is substantially equal to the width and/or depth of the grooves. A preferred embodiment of the prosthesis of the present invention is a femoral stem for a hip joint which has a plurality of grooves, extending generally transversely to a longitudinal axis of the stem, formed on proximal portions of selected surfaces of the stem. Distal portions of the stem surfaces are relatively smooth. The grooves are oriented approximately perpendicularly to a line of force transmitted from the head to the shank of the stem. The grovoes preferably lie in planes which intersect the longitudinal axis of the shank at an angle of approximately 60°–80°. In the illustrated embodiment, additional grooves which extend generally longitudinally are provided in a proximal portion of the medial surface of the stem. All of the grooves in the stem surfaces are preferably of equal depth and width, and are preferably uniformly spaced.

24 Claims, 1 Drawing Sheet

GROOVED ENDOPROSTHESIS

BACKGROUND AND SUMMARY OF THE INVENTION

This invention relates generally to a grooved endoprosthesis, and more specifically to the use of a Particular arrangement and type of groove pattern to promote biological fixation of endoprostheses of various types. A Particular application of the groove pattern of the present invention, as used on a femoral stem of a hip joint prosthesis, is also disclosed.

Component loosening is one of the primary reasons for failure of cemented hip arthroplasties. In the past decade, attempts have been made to correct this problem by providing for biological fixation of the components. A common technique involves use of a porous coating on the surface of the component to encourage bone ingrowth for fixation purposes. A commonly used porous surface for cementless fixation is sintered (cobalt-chromium). This surface is produced by the high temperature sintering of spherical alloy beads to a similar alloy substrate. The process forms metallurgical bonds between the spherical beads and the underlying substrate. Other implants employ surfaces of plasma-sprayed titanium. This surface is produced by spraying heated powdered titanium alloy onto a titanium alloy substrate. Unlike the sintered Co-Cr surface, which has relatively well-defined pores, the titanium plasma spray coating forms a somewhat irregular porous surface which provides channels for bone ingrowth, but which lacks a three-dimensional interconnecting system.

The process of manufacturing either of these porous coated surfaces is difficult and expensive. Strict quality control requirements result in only a percentage of the implants actually produced by either process being acceptable for clinical use. There is also considerable concern about the negative effect which the sintering process may have on the crystalline structure of the underlying substrate.

Another problem which has been observed in the use of known hip joint systems relates to the proper distribution of stresses within the prosthesis and throughout the surrounding bone. If too little stress is applied to the bone, resorption can occur leading to atrophy of the affected area. Too much stress may also lead to resorption and atrophy, or may result in undesirable hypertrophy of the affected area. In some prior art femoral stem designs, too much force is transmitted through the relatively rigid stem to the distal portion, resulting in hypertrophy of the bone surrounding the distal portion, and atrophy of the bone surrounding the proximal portion of the stem. Accordingly, there exists a need for an improved hip joint prosthesis which addresses these and other problems of prior hip joint designs.

An object of the present invention is to provide an improved arrangement of grooves on an implantable prosthesis which has been found to be especially effective in promoting biological fixation of the prosthesis through the mechanism of bone ingrowth.

Another object of the present invention is to provide a femoral stem for a hip joint prosthesis which provides for relatively strong fixation of the proximal end of the stem to the femur, and which provides for relatively weak fixation of the distal end of the stem.

Another object of the present invention is to provide a femoral stem for a hip joint prosthesis which has precisely controlled mechanical and metallurgical properties, and which provides a precisely dimensioned surface for bone fixation.

Yet another object of the present invention is to provide a femoral stem for a hip joint prosthesis which is relatively easy and inexpensive to manufacture.

Still another object of the present invention is to provide a femoral stem for a hip joint prosthesis which can be more readily removed from the bone in the event resection becomes necessary.

These and other objects are attained in a hip joint prosthesis which includes a femoral stem which has a head and an elongated shank. The head is adapted to cooperate with either a natural acetabulum or a prosthetic acetabulum. The shank has a proximal end adjacent the head and a distal end which extends longitudinally into the intramedullary canal of the femur. The shank further has anterior (front), posterior (back), lateral (outside), and medial (inside) surfaces. A plurality of grooves extending generally transversely to the longitudinal axis of the shank are formed on proximal portions of selected surfaces of the shank, while distal portions of these selected surfaces are left relatively smooth. In a preferred embodiment, these grooves are substantially parallel grooves formed in the anterior and posterior surfaces of the shank. The grooves on the anterior and posterior surfaces are preferably oriented approximately perpendicularly to a line of force transmitted from the head to the shank of the femoral stem. The grooves preferably lie in planes which intersect the longitudinal axis of the shank at an angle of approximately 60°-80°, as measured from a point on the axis which lies above the proximal end of the shank along an arc which extends toward the lateral surface of the shank, with an especially preferred orientation of the grooves lying in planes which intersect the longitudinal axis at an angle of approximately 70° as measured from a point on the axis which lies above the proximal end of the shank along an arc which extends toward the lateral surface of the shank.

An especially preferred embodiment of the invention includes a plurality of substantially parallel grooves in the proximal portion of the medial surface. These grooves preferably extend generally longitudinally along the proximal portion of the medial surface, and are especially effective in providing resistance to torque or rotational forces on the stem.

The grooves formed in the anterior, posterior and medial surfaces are substantially equal in depth and width, and are substantially uniformly spaced apart by a distance which is preferably equal to the depth and width of the grooves. The width of the grooves ranges from approximately 0.014" to 0.021" (350 microns to 535 microns), with an especially preferred width being approximately 0.0197" (500 microns). The preferred depth of the grooves ranges from approximately 0.015" to 0.025" (380 microns to 635 microns). Grooves having these dimensions in width, depth and spacing have been found to be particularly effective in promoting biological fixation of endoprostheses by tissue ingrowth. Such grooves are well-suited for use with the femoral stem described in detail in this application, and for other types of implantable prostheses as well. In the femoral stem described below, approximately 25 grooves are spaced along the proximal $\frac{1}{4}$-$\frac{1}{3}$ of the anterior and posterior surfaces of the shank, while approximately three grooves are formed in the proximal portion of the medial surface.

The present invention provides for a macro-interlocking or fixation of the prosthesis to the surrounding bone. The grooved surface of the prosthesis can be precisely manufactured without adversely affecting the properties of the substrate material. The machining process is repeatable and relatively efficient, resulting in a decrease in both expense and difficulty in the manufacture of the prosthesis when compared to several prior art devices.

The femoral stem prosthesis of the present invention provides strong proximal fixation of the stem to better and more naturally distribute stresses throughout the femur. Prior art designs which allow for fixation of the stem throughout substantially all or most of its length provide for the transmission of too much stress through the stem to the distal portion of the shank. This lead to atrophy in the proximal portion of the femur, and undesired hypertrophy in the area of the femur surrounding the distal portion of the stem. The stem of the present invention distributes the stresses in the proximal portion of the femur, preventing resorption and atrophy which may otherwise result. In the event resection of the stem is necessary, the design of the present invention allows easier access to the interlocked area, and will result in the disturbance of a smaller portion of the femur than might otherwise occur in the case of a distally interlocked shank.

Other objects, advantages and novel features of the present invention will become apparent from the following detailed description of the invention when considered in conjunction with the accompanying drawings.

DETAILED DESCRIPTION OF THE DRAWINGS

Figure 1:
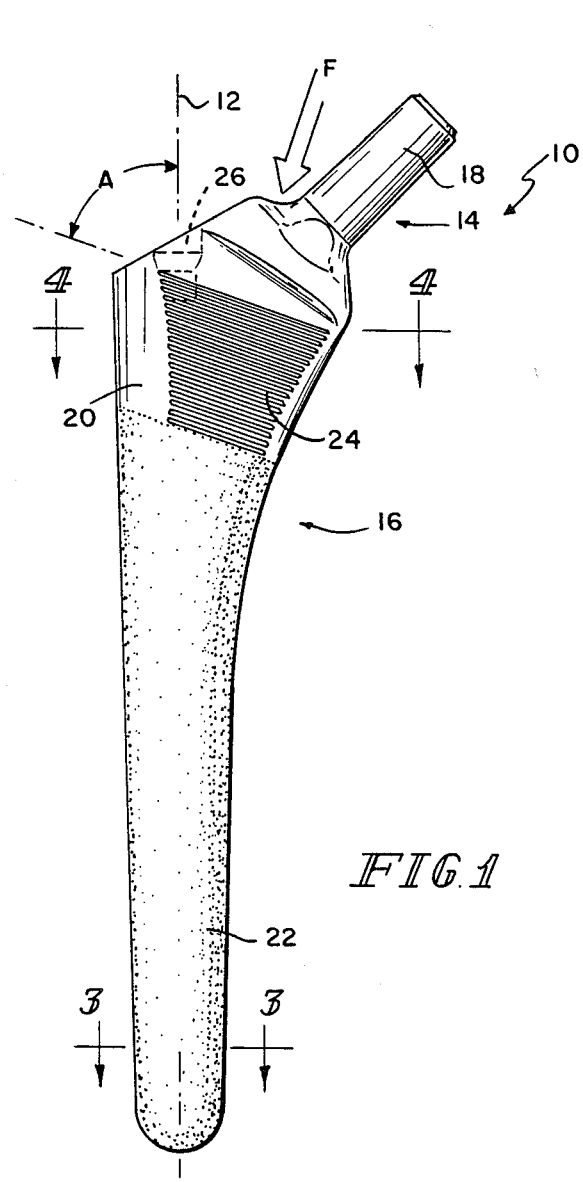
FIG. 1 shows a plan view of the anterior (or posterior) surface of a femoral stem constructed in accordance with the present invention.

FIG. 1 shows a plan view of the anterior surface of a femoral stem 10 which is constructed in accordance with the Present invention. It should be noted that, in this preferred embodiment of the invention, the anterior and posterior surfaces of femoral stem 10 are identical in terms of the features which are relevant to the present invention. In other words, the posterior surface of stem 10 would appear identical to the surface shown in FIG. 1, except for a 180° rotation of the stem around longitudinal axis 12. Accordingly, a plan view of the posterior surface of stem 10 is not shown in a separate drawing.

Femoral stem 10 comprises head portion 14 and shank portion 16. Head 14 includes a cone 18 onto which a spherical ball (not shown) having a conical bore is fitted. The spherical ball interacts with the natural acetabulum or a prosthetic acetabulum to provide for joint movement.

Shank 16 has a proximal surface portion 20 immediately adjacent head 14, and a distal surface portion 22. A plurality of grooves 24 are formed in proximal surface portion 20, extending in a generally transverse relationship with longitudinal axis 12. In preferred embodiments of the invention, a plane projected from grooves 24 intersects axis 12 at an angle A of approximately 60° to 80°, with the preferred angle of intersection being approximately 70°. This results in grooves 24 being oriented approximately perpendicularly to a line of force F which is transmitted from head 14 to shank 16. This preferred orientation of grooves 24 provides for the maximum resistance to force F and for the optimal distribution of stresses to the surrounding bone tissue of the femur. Distal surface portion 22 is relatively smooth and grooveless to provide for relatively weak fixation to the surrounding bone tissue, as compared to grooved proximal surface portion 20. In a Preferred embodiment, distal surface portion 22 is blastfinished with No. 30 aluminum oxide grit. This provides a surface which is slightly rougher than proximal surface portion 20 (which is preferably blast-finished with glass beads), but which does not provide for any substantial ingrowth of bone or other substantial fixation to the femur.

Proximal surface portion 20 of shank 16 is preferably provided with approximately twenty-five grooves 24 which are generally parallel and equally spaced and which are dimensioned so as to readily accept the ingrowth of bone tissue, as will be described more fully below. A threaded opening 26 is provided in the top surface of the stem to allow for attachment of insertion and extraction tools.

Figure 2:
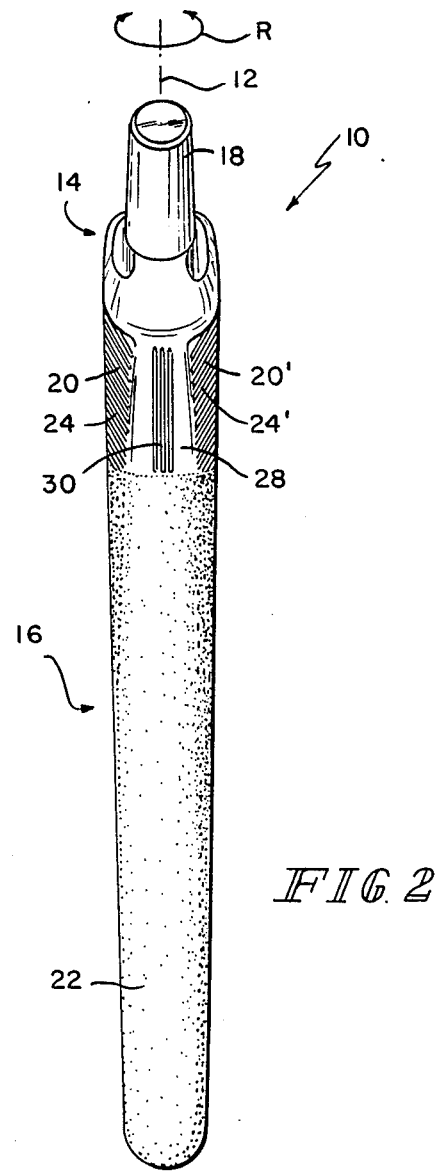
FIG. 2 shows a plan view of a medial surface of a femoral stem constructed in accordance with the present invention.

FIG. 2 shows a plan view of the medial surface of femoral stem 10. Also visible in FIG. 2 is proximal surface portion 20' of the posterior side of stem 10, and grooves 24' which are formed in surface portion 20' in identical fashion to grooves 24 on anterior surface 20. As can be seen in FIG. 2, proximal surface portions 20 and 20' are non-parallel surfaces which tend to converge as they approach the medial surface of stem 10, and diverge as they approach the lateral surface.

FIG. 2 shows proximal medial surface 28 which has a plurality of longitudinal grooves 30 formed thereon. As described more fully below, grooves 30 are also dimensioned so as to readily accept the ingrowth of bony tissue to anchor the Proximal portion of stem 10 firmly into position. The longitudinal orientation of grooves 30 result in the impartation of a high degree of resistance to torque or rotational forces (represented by arrow R) which may be imposed on the implanted stem, since grooves 30 are perpendicular to such forces. It should be noted at this point that grooves 24 and 24' also impart some resistance to rotational forces since, as is apparent from FIG. 2, the angle of orientation of grooves 24 and 24' varies from 20° to 40° from the horizontal line along which such rotational forces would act.

Figure 3:
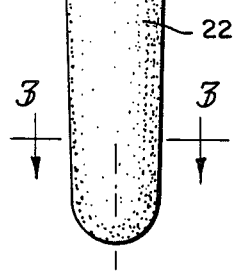
FIG. 3 shows a cross-section of the femoral stem of FIG. 1 taken along line 3—3.
Figure 4:
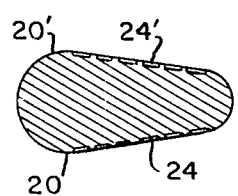
FIG. 4 shows a cross-section of the femoral stem of FIG. 1 taken along line 4—4.

FIG. 3 shows a cross-sectional view along line 3—3 in the vicinity of distal surface portion 22 of shank 16. FIG. 4 shows a cross-sectional view along line 4—4 in the vicinity of proximal surface portion 20 of shank 16. As is the case in FIG. 2, FIG. 4 illustrates the shape of the prosthesis in the proximal region (i.e., surface portions 20 and 20' converge when approaching the medial side and diverge when approaching the lateral side of the prosthesis).

Figure 5:
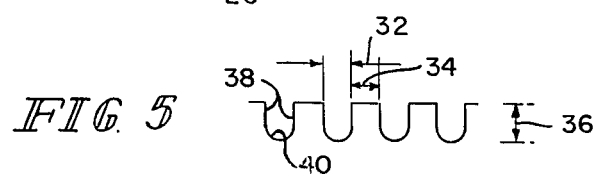
FIG. 5 shows a cross-section through a typical portion of a grooved surface conforming to the design of the present invention.

FIG. 5 shows the details of the grooves used in the preferred embodiment of the invention. These grooves are specifically sized so as to achieve an effective macrointerlock with the surrounding bone tissue in the shortest possible time. The width 32 of each groove is preferably the same and ranges from 0.014" to 0.021" (350 microns to 535 microns). An especially preferred width is approximately 0.0197" (500 microns). The distance 34 between adjacent grooves is preferably the same, and is preferably equal to the width 32 of each groove. The depth 36 of each groove is also preferably the same, and preferably ranges from 0.015" to 0.025" (380 microns to 635 microns). Side walls 38 of the grooves are preferably parallel, while end wall 40 is radial. As noted, grooves having these characteristics and dimensions are especially well-suited for promoting biological fixation of various types of endoprostheses.

In the particular prosthesis illustrated in the Drawings, all grooves on the anterior, posterior and medial surfaces are substantially identical in width, depth and spacing. The uniformity and precise dimensioning of the grooves on the anterior, posterior, and medial surfaces helps promote and attain relatively strong fixation of proximal surface portion 20, and an even distribution and transmission of stresses to the surrounding bone.

The prostheses of the present invention are preferably made from a well-known titanium alloy (Ti 6Al 4V) which has been found to be biologically compatible with living tissue and very well-suited for use in implantable prosthesis components. Other acceptable materials from which prostheses may be made include stainless steel and a Co-Cr (cobalt-chromium) alloy.

From the preceding description of the preferred embodiments, it is evident that the objects of the invention are attained, and although the invention has been described and illustrated in detail, it is to be clearly understood that the same is by way of illustration and example only and is not to be taken by way of limitation. The spirit and scope of the invention are to be limited only by the terms of the appended claims.

What is claimed is:

1. A hip joint prosthesis comprising a femoral stem having a head and an elongated shank, the head being adapted to cooperate with a natural acetabulum or a prosthetic acetabulum, the shank having a proximal end adjacent the head and a distal end and a longitudinal axis extending from the proximal end to the distal end, and said shank having an anterior surface, a posterior surface, a lateral surface and a medial surface, wherein a plurality of grooves extending generally transversely to said longitudinal axis are formed on proximal portions of selected surfaces of the shank, and wherein distal portions of said selected surfaces are relatively grooveless, and wherein said plurality of grooves are substantially parallel grooves formed in the anterior and posterior surfaces, and wherein a plurality of grooves are formed in said medial surface, and wherein said grooves in the medial surface extend generally longitudinally along a proximal portion of said medial surface.

2. A hip joint prosthesis according to claim 1, wherein at least a portion of said grooves lie in planes which intersect the longitudinal axis of the shank at an angle of approximately 60°–80°, as measured from a point on the axis which lies above the proximal end of the shank along an arc which extends toward the lateral surface of the shank.

3. A hip joint prosthesis according to claim 1, wherein at least a portion of said grooves lie in planes which intersect the longitudinal axis of the shank at an angle of approximately 70°, as measured from a point on the axis which lies above the proximal end of the shank along an arc which extends toward the lateral surface of the shank.

4. A hip joint prosthesis according to claim 1, wherein at least a portion of said grooves in the medial surface are substantially equal in depth and width and are substantially uniformly spaced apart.

5. A hip joint prosthesis according to claim 4, wherein the width and depth of said grooves in the medial surface and the space between adjacent grooves in the medial surface are substantially equal.

6. A hip joint prosthesis according to claim 1, wherein at least a portion of said grooves are substantially equal in depth and width, and are substantially uniformly spaced apart.

7. A hip joint prosthesis according to claim 6, wherein the width and depth of said grooves and the space between adjacent grooves are substantially equal.

8. A hip joint prosthesis according to claim 1, wherein at least a portion of said grooves have a width which ranges from 350–535 microns.

9. A hip joint prosthesis according to claim 1, wherein at least a portion of said grooves have a width of approximately 500 microns.

10. A hip joint prosthesis according to claim 1, wherein at least a portion of said grooves have a depth which ranges from 380–635 microns.

11. A hip joint prosthesis according to claim 1, wherein at least a portion of said grooves have parallel side walls, having a length substantially equal to the width of said grooves, and an arcuate end wall.

12. A hip joint prosthesis according to claim 1, wherein the femoral stem is formed from a biologically compatible titanium alloy.

13. A hip joint prosthesis according to claim 1, wherein, in the proximal one-third of the shank, the anterior and posterior surfaces are non-parallel surfaces which tend to converge in a direction which moves from the lateral surface to the medial surface.

14. A hip joint prosthesis comprising a femoral stem having a head and an elongated shank, the head being adapted to cooperate with a natural acetabulum or a prosthetic acetabulum, the shank having a proximal end adjacent the head and a distal end and a longitudinal axis extending from the proximal end to the distal end, and said shank having an anterior surface, a posterior surface, a lateral surface and a medial surface, wherein a plurality of substantially parallel, transversely extending grooves are formed on proximal portions of the anterior and posterior surfaces of the shank, and wherein a plurality of substantially parallel, longitudinally extending grooves are formed on a proximal portion of the medial surface, and wherein said transversely extending grooves on the anterior and posterior surfaces, and said longitudinally extending grooves on the medial surface lie adjacent substantially common portions of the longitudinal axis of the shank.

15. A hip joint prosthesis according to claim 14, wherein the distal end of the shank has a relatively smooth surface.

16. A hip joint prosthesis according to claim 14, wherein said grooves formed on the anterior and posterior surfaces lies in planes which intersect the longitudinal axis of the shank at an angle of approximately 60°–80°, as measured from a point on the axis which lies above the proximal end of the shank along an arc which extends toward the lateral surface of the shank.

17. A hip joint prosthesis according to claim 14, wherein said grooves formed on the anterior and posterior surfaces lie in planes which intersect a longitudinal axis of the shank at an angle of approximately 70°, as measured from a point on the axis which lies above the proximal end of the shank along an arc which extends toward the lateral surface of the shank.

18. A hip joint prosthesis according to claim 14, wherein at least a portion of said grooves in the anterior and posterior surfaces are substantially equal in depth and width, and are substantially uniformly spaced apart.

19. A hip joint prosthesis according to claim 18, wherein the width and depth of said grooves and the space between adjacent grooves are substantially equal.

20. A hip joint prosthesis according to claim 19, wherein said grooves in the medial surface lie in planes which extend generally parallel to said longitudinal axis and are substantially equal in depth and width to said grooves in the anterior and posterior surfaces, and are substantially uniformly spaced apart.

21. A hip joint prosthesis according to claim 19, wherein each of said grooves in the anterior and posterior surfaces has a width which ranges from 350–535 microns.

22. A hip joint prosthesis according to claim 14, wherein each of said grooves formed in the anterior and posterior surfaces has a width of approximately 500 microns.

23. A hip joint prosthesis according to claim 14, wherein each of said grooves in the anterior and posterior surfaces has a depth which ranges from 380–635 microns.

24. A hip joint prosthesis according to claim 14, wherein each of said grooves in the anterior and posterior surfaces has parallel side walls, having a length substantially equal to the width of said grooves, and an arcuate end wall.

* * * * *